US010052394B2

(12) United States Patent
Butts et al.

(10) Patent No.: US 10,052,394 B2
(45) Date of Patent: Aug. 21, 2018

(54) MICROBUBBLE TETHER FOR DIAGNOSTIC AND THERAPEUTIC APPLICATIONS

(71) Applicant: GENERAL ELECTRIC COMPANY, Schenectady, NY (US)

(72) Inventors: Matthew David Butts, Rexford, NY (US); Jason William Castle, Esperance, NY (US); Andrew Soliz Torres, Niskayuna, NY (US); Jeannette Christine Roberts, Brunt Hills, NY (US); Binil Itty Ipe Kandapallil, Mechanicsville, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 631 days.

(21) Appl. No.: 14/550,689

(22) Filed: Nov. 21, 2014

(65) Prior Publication Data

US 2016/0144059 A1    May 26, 2016

(51) Int. Cl.
*A61K 49/22* (2006.01)
*A61K 9/00* (2006.01)
*A61K 9/50* (2006.01)

(52) U.S. Cl.
CPC .......... *A61K 49/223* (2013.01); *A61K 9/0009* (2013.01); *A61K 9/5052* (2013.01)

(58) Field of Classification Search
CPC ... A61K 49/223; A61K 9/5052; A61K 9/0009
See application file for complete search history.

(56) References Cited

U.S. PATENT DOCUMENTS

| | | | |
|---|---|---|---|
| 5,315,998 A | 5/1994 | Tachibana et al. | |
| 5,439,686 A | 8/1995 | Desai et al. | |
| 5,876,696 A | 3/1999 | Quay | |
| 6,193,951 B1 | 2/2001 | Ottoboni et al. | |
| 6,193,952 B1 | 2/2001 | Kabalnov et al. | |
| 6,231,834 B1 | 5/2001 | Unger et al. | |
| 6,245,318 B1 | 6/2001 | Klibanov et al. | |
| 6,245,747 B1 | 6/2001 | Porter et al. | |
| 6,413,215 B1 | 7/2002 | Wu et al. | |
| 6,416,739 B1 | 7/2002 | Rogerson et al. | |
| 6,537,814 B1 | 3/2003 | Porter et al. | |
| 6,716,412 B2 | 4/2004 | Unger | |
| 6,723,303 B1 | 4/2004 | Quay | |
| 6,776,761 B2 | 8/2004 | Ottoboni et al. | |
| 6,797,257 B2 | 9/2004 | McDonald et al. | |
| 6,896,659 B2 | 5/2005 | Conston et al. | |
| 6,979,296 B2 | 12/2005 | See | |
| 6,986,740 B2 | 1/2006 | Dees et al. | |
| 7,015,352 B2 | 3/2006 | Mills | |
| 7,083,778 B2 | 8/2006 | Schneider et al. | |
| 7,115,583 B2 | 10/2006 | Porter et al. | |
| 7,198,949 B2 | 4/2007 | Porter et al. | |
| 7,211,248 B2 | 5/2007 | Davidson | |
| 7,358,226 B2 | 4/2008 | Dayton et al. | |
| 8,012,457 B2 | 9/2011 | Walovitch et al. | |
| 8,685,372 B2 | 4/2014 | Tsien et al. | |
| 2003/0044353 A1 | 3/2003 | Weissleder et al. | |
| 2003/0216337 A1 | 11/2003 | Hallahan | |
| 2007/0092447 A1* | 4/2007 | Padilla De Jesus | A61B 5/0059 424/9.1 |
| 2007/0104649 A1 | 5/2007 | Fischer et al. | |
| 2008/0200862 A1 | 8/2008 | Unger et al. | |
| 2010/0048890 A1 | 2/2010 | Grotzfeld et al. | |
| 2010/0143241 A1 | 6/2010 | Johnson et al. | |
| 2010/0158815 A1 | 6/2010 | Wang et al. | |
| 2011/0182979 A1 | 7/2011 | Shimoda et al. | |
| 2011/0293530 A1 | 12/2011 | Hecht et al. | |
| 2013/0072854 A1 | 3/2013 | Mohan et al. | |

FOREIGN PATENT DOCUMENTS

| | | |
|---|---|---|
| WO | 2011053803 A2 | 5/2011 |
| WO | 2014021678 A1 | 2/2014 |
| WO | 2014055253 A1 | 4/2014 |

OTHER PUBLICATIONS

Klibanov Alexander L et al., "Microbubble Contrast Agents: Targeted Ultrasound Imaging and Ultrasound-Assisted Drug-Delivery Applications", Investigative Radiology, vol. 41—Issue 3—pp. 354-362, Mar. 2006.

Dijkmans et al., "Microbubbles and ultrasound: from diagnosis to therapy", European Heart Journal Cardiovascular imaging, vol. 5, Issue 4, pp. 245-246, pp. 571-587, 2004.

PCT Search Report and Written Opinion issued in connection with corresponding PCT Application No. PCT/EP2015/077315 dated Jan. 25, 2016.

* cited by examiner

*Primary Examiner* — Michael G Hartley
*Assistant Examiner* — Leah H Schlientz
(74) *Attorney, Agent, or Firm* — GE Global Patent Operation; Pabitra Chakrabarti (57) ABSTRACT

The present disclosure relates to a composition of albumin microbubbles to which are bound one or more moieties that exhibit a binding preference for the albumin microbubbles relative to free, native HSA. Production of the albumin microbubble composition and use of the albumin microbubble composition in ultrasound mediated delivery of therapeutic or diagnostic agents is also discussed.

7 Claims, 13 Drawing Sheets

MICROBUBBLE TETHER FOR DIAGNOSTIC AND THERAPEUTIC APPLICATIONS

BACKGROUND

The subject matter disclosed herein relates to the use of microbubble compositions in diagnostic or therapeutic applications.

A variety of therapeutic agents or drugs are not commercially or medically viable due to one or more of adverse side effects, poor solubility in blood, or high cost. To address certain of these failings, delivery systems such as ultrasound microbubble (USMB) mediated delivery systems have been developed. In such a system, a gas-filled microbubble is associated with a treatment agent of interest. Under treatment conditions, the gas-filled microbubbles undergo cavitation in response to the application of ultrasonic energy at a targeted site (i.e., anatomic region) of interest. This cavitation event results in microbubble destruction (inertial cavitation) and is, presumably, accompanied by a shock wave that leads to the formation of transient pores in the membranes of surrounding tissues and cells. The transient pores allow the treatment agent to gain access to the tissues to be treated. In other scenarios, ultrasound results in stable cavitation rather than inertial cavitation, which can also lead to enhanced delivery of drugs to tissues or cells. Such approaches have been investigated with possible future applications involving the targeted delivery of small molecule drugs, oligonucleotides, and plasmid DNA (pDNA), such as to a patient.

Delivery of therapeutic agents can be significantly enhanced in the presence of microbubbles upon application of ultrasound. Generally, agent pharmacokinetic properties and clearance mechanisms are key drivers behind delivery to tissue and cells. Binding between the microbubble and the agent of interest can affect the efficiency of agent delivery to a site of interest by, for example, enhancing in vivo stability, manipulating agent biodistribution characteristics, or other mechanisms. The nature and extent of such binding relationships, and their effect on delivery, however, have generally not been thoroughly researched and are poorly understood. It may be desirable, therefore, to develop a more suitable USMB mediated drug delivery system and associated delivery agents.

BRIEF DESCRIPTION

In one embodiment, a composition is provided. The composition includes a microbubble comprising an albumin shell, and a moiety bound to the microbubble. The moiety binds preferentially to the microbubble relative to native albumin.

In an additional embodiment, a composition is provided. The composition includes an albumin microbubble comprising an albumin shell. The composition also includes a therapeutic or diagnostic agent, and a cyanine 5 derivative linking the albumin microbubble and the therapeutic or diagnostic agent.

In a further embodiment, a method is provided. The method includes the mixing at room temperature of an albumin microbubble composition and the drug agent or moiety-bound drug agent wherein the drug agent or the moiety-bound drug agent binds preferentially to the microbubble relative to native albumin.

In yet a further embodiment, an ultrasound-based treatment method is provided. The method includes the act of introducing an albumin microbubble composition into a patient. The albumin microbubble composition comprises: an albumin shell, a molecule of interest, and a moiety binding the molecule of interest to the albumin shell. The moiety preferentially binds to the albumin shell relative to free, native human serum albumin. A further act of the method is then to direct ultrasonic energy at an anatomic region of interest to cause cavitation of the albumin microbubbles at the anatomic region of interest.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Certain aspects of the present disclosure relate to a diagnostic or therapeutic microbubble composition that includes a moiety that functions as a binding tether to albumin microbubbles. The moiety may be attached to a pharmacological or diagnostic agent, such as a therapeutic agent or a diagnostic composition that may facilitate imaging or other diagnostic procedures at a target location.

Further, in certain embodiments, the moiety may also function as an optical tracer (e.g., may fluoresce) and, in such embodiments, the optical tracing may be leveraged for diagnostic purposes, e.g., as an optical probe. A mediated agent delivery system suitable for in vivo use with such compositions may, therefore, include: 1) albumin microbubbles, 2) one or more moieties that show a binding preference for the albumin microbubbles (e.g., Optison™) relative to free native human serum albumin, and 3) ultrasound energy for targeted delivery of the therapeutic or diagnostic composition. In some embodiments, the one or more moieties may be molecules used to functionalize a therapeutic or diagnostic composition of interest. In other embodiments, the moiety may be an intrinsic group of the therapeutic or diagnostic composition of interest such that the composition itself exhibits the binding preference for the albumin microbubbles relative to free native human serum albumin.

With respect to the albumin microbubbles, these microbubbles may be derived from human serum albumin (HSA) or from other suitable biocompatible albumin sources, including synthetic or synthesized albumin. An example of one such albumin microbubble source is Optison™ albumin shell microbubbles. Optison™, or other suitable microbubble forming media, may be derived from HSA but may be distinct from free, native HSA found in vivo in the body. By way of example, in the context of Optison™ microbubbles, these microbubbles have an HSA shell surrounding a perfluoropropane core. In some embodiments, a suitable microbubble may have a mean diameter in the range of about 3-4.5 µm (e.g., between about 1 µm and about 10 µm). The albumin present in gas-filled, albumin microbubble compositions such as Optison™ or other suitable compositions may be distinct from HSA found in vivo for one or more of the following reasons: it may be partially denatured, it may be partially crosslinked or the albumin may be present in a different ratio of one or more protein conformations relative to native HSA.

As noted above, in certain embodiments the one or more moieties that attach to the microbubble may exhibit a binding preference for albumin microbubbles relative to free native human serum albumin. As discussed herein, in certain embodiments molecules that show a binding preference to albumin microbubbles relative to free, native HSA can be provided as functional groups on drugs, binding them to the microbubbles and enabling efficient drug delivery in vivo upon application of ultrasound energy. In certain instances, the moiety may intrinsically be present on the drug of interest, and thus need not be added in a separate step. In one embodiment, the moiety component may be a pegylated or non-pegylated cyanine 5 (Cy5) derivative that can be used to "tether" a therapeutic or diagnostic agent to the microbubbles. For example, a Cy5 derivative acting as a tether to a microbubble may be functionalized with a therapeutic agent, such as a small molecule drug, an oligonucleotide (such as siRNA), or a large molecule (such as a plasmid DNA).

With the preceding in mind, present approaches may be used to address drug delivery issues related to adverse side effects, poor solubility in blood, or high cost. In one implementation, by binding a therapeutic agent to a microbubble (such as using a tether), a complex is formed that reduces the drug's bioavailability as it circulates in vivo, until it is released at the target site upon sonication. This has the effect of reducing adverse side effects. The complex formation can also enhance solubility, as a microbubble can carry multiple copies of a drug that might otherwise exhibit poor solubility. Overall cost is reduced because the efficiency of drug delivery can in principle be significantly enhanced upon binding to bubbles by increasing local drug concentration at the site of ultrasound delivery.

Further, and as noted above, in certain embodiments, the moiety (e.g., Cy5 derivatives) fluorescently tags the microbubble to which they are attached. In such embodiments, the Cy5 derivative may alternatively or additionally function as an optical tracer, allowing localization or visualization of the microbubbles through non-invasive imaging.

Figure 1:
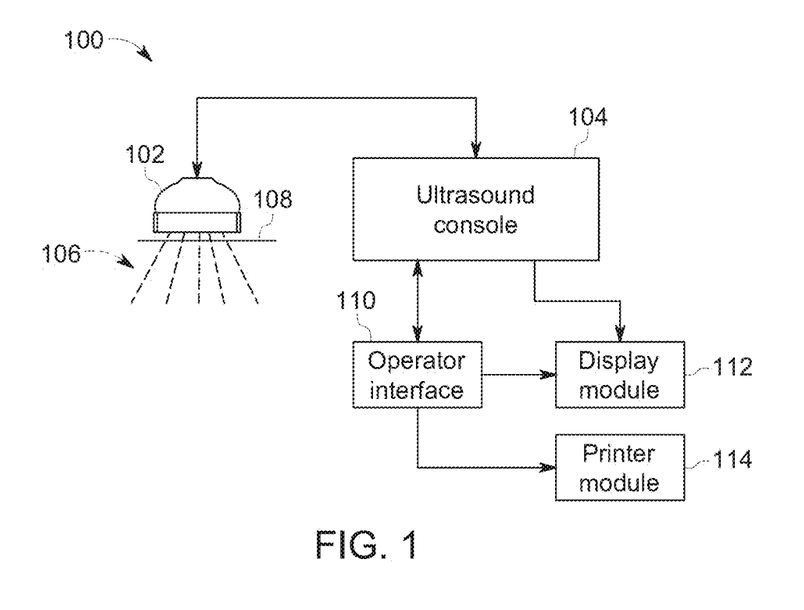
FIG. 1 depicts an ultrasound system suitable for use in an ultrasound microbubble mediated drug delivery system, in accordance with aspects of the present disclosure.

With the preceding in mind, and turning to FIG. 1, an example of ultrasound system components that may be present in an USMB mediated drug delivery system 100 is depicted. As will be appreciated, such components may correspond to those found in a conventional ultrasound imaging system and the system may in practice be used to image the target tissue in conjunction with the mediated delivery of a therapeutic agent. In the depicted example, the ultrasound system includes an ultrasound probe 102 and an ultrasound console 104 suitable for generating and receiving ultrasound signals via the probe 102. In certain embodiments, the ultrasound console 104 may include beam-formers and image reconstruction and processing circuitry used to direct the ultrasonic energy 106 into the tissue 108 of the patient and to reconstruct the return signals measured at the probe 102. For example, the ultrasound console 104 may control the strength, beam focus or forming, duration, phase, and frequency of the ultrasound signals transmitted by the ultrasound probe 102, and may decode the information contained in the plurality of reflected ultrasound signals from the tissue to a plurality of discernible electrical and electronic signals. In USMB embodiments, the ultrasonic energy 106 may, within the targeted tissue 108, facilitate the release of a therapeutic or diagnostic agent at an anatomic location of interest. The return signals may be processed at the console 104 to generate images of the anatomic region of interest underlying the probe 102.

The ultrasound system 100 may also include an operator interface 110 allowing a user to interact with and control the console 104. The operator interface 110 may include a keyboard, a mouse, and other user interaction devices. The operator interface 110 can be used to customize a plurality of settings for an USMB procedure, to effect system level configuration changes, and to allow operator activation and operation of the ultrasound system 100.

In the depicted example, the operator interface 110 is connected to the ultrasound console 104, a display module 112, and a printer module 114, some or all of which may be provided as an ultrasound workstation. The display module 112 receives image information from the ultrasound console 104 and presents the image of the objects underlying the ultrasound probe 102. The printer module 114 is used to produce a hard copy of the ultrasound image in either gray-scale or color. In general, the reflected ultrasound signals and corresponding images convey information about thickness, size, and location of various tissues, organs, tumors, and anatomical structures in relation to transmitted ultrasound signals.

Figure 2:
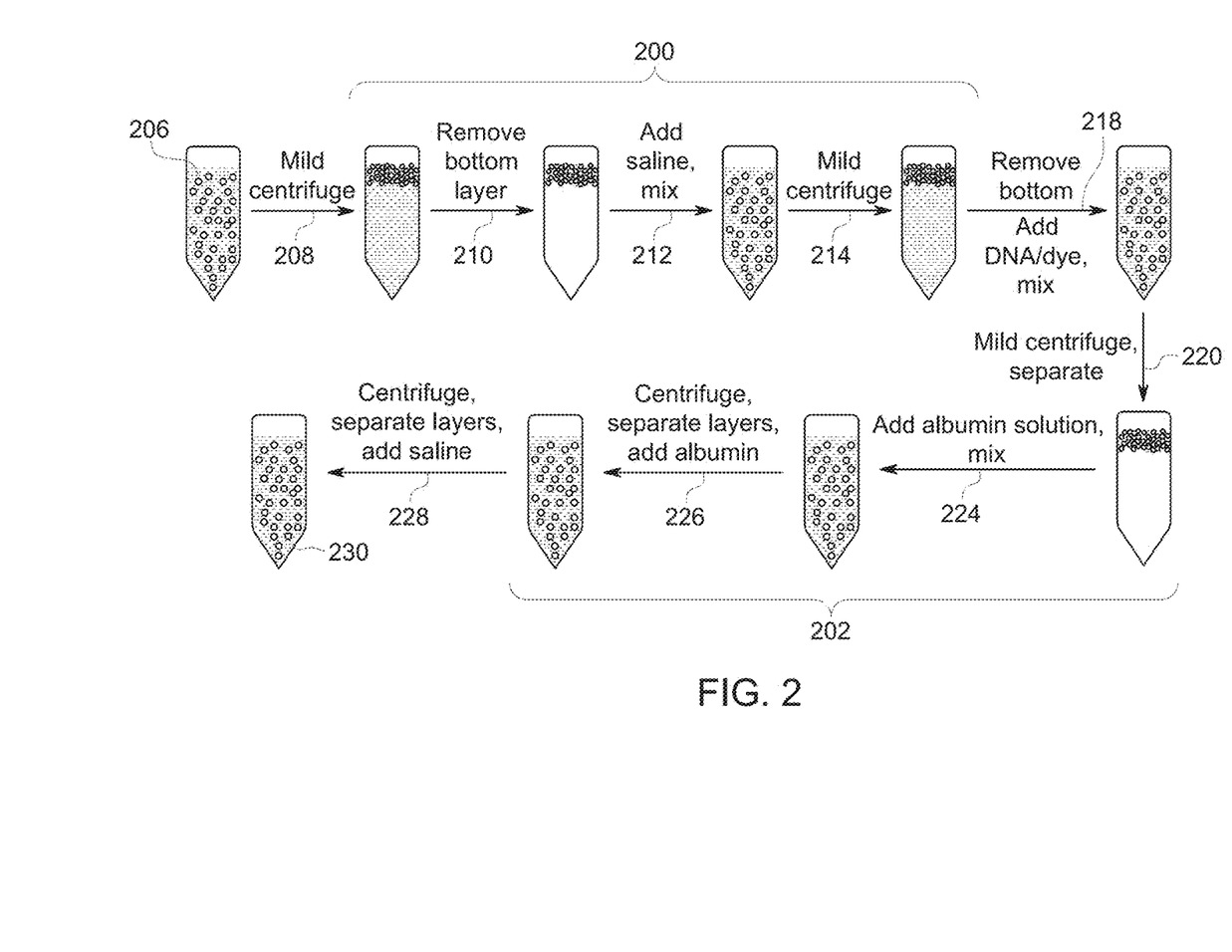
FIG. 2 depicts a sample preparation process flow, in accordance with one aspect of the present disclosure.

With the preceding in mind, certain studies related to the present subject matter are discussed below. With respect to the existence of moieties having a binding preference for albumin microbubbles relative to free, native HSA, a study was performed to characterize the binding affinity between the ApoA-I pDNA and albumin microbubbles (e.g., Optison™ bubbles). FIG. 2 illustrates the sample preparation method used in this study. In this example, three distinct operations are shown. In the first operation (steps 200), bubble separation and a wash to remove free albumin were performed. In the second operation (step 218), the washed bubbles were mixed with the pDNA/dye binding solution. In the third operation (steps 202), two saline or two native human serum albumin washes were performed followed by saline reconstitution to afford the final composition for analysis.

With respect to the first operation, in this example, Optison™ was used as the microbubble composition, and it was washed once with saline (step 212) to remove free HSA present in the commercial product. In particular, in the depicted example, the microbubble product 206 was initially centrifuged (step 208), the bottom layer removed (step 210), saline added and mixed (step 212), followed by an additional centrifugation (step 214). After centrifugation the bottom layer was again removed, and to the remaining albumin microbubbles was mixed the DNA/dye composition (step 218).

With respect to the DNA/dye composition, in this study, pDNA was first mixed with propidium iodide (PI), which fluoresces when intercalated into the DNA structure but does not fluoresce as the result of any interaction with the microbubble (should one exist). As noted above, the pDNA/dye solution was mixed with the albumin microbubbles (step 218) and the product centrifuged (step 220). The resulting microbubble/DNA/dye product was washed twice (steps 224 and 226) with a 9.5 mg/mL native HSA solution followed by a saline reconstitution (step 228) to yield the final analytic product 230. In other experimental runs, different washing sequences were employed.

In this study, the affinity of the pDNA for the microbubble as a function of bubble washing was assessed using fluorescence microscopy and flow cytometry. No evidence for statistically relevant binding between the pDNA and the albumin microbubble was observed. In particular, any binding interaction between the pDNA and the microbubbles was sufficiently weak that a simple microbubble separation followed by a saline wash was sufficient to remove the pDNA.

In contrast, other studies were performed in which the agent in question was found to bind to the microbubble. For example, in one set of studies the model agents investigated were derivatives of cyanine 5 (Cy5), such as pegylated Cy5 dyes. Generally, pegylated and non-pegylated agents comprising hydrophobic Cy5 moieties were observed to be good binders to albumin microbubbles, whereas agents comprising highly sulfonated Cy5 groups (Cy5**) were observed to be poor binders to albumin microbubbles.

Figure 3:
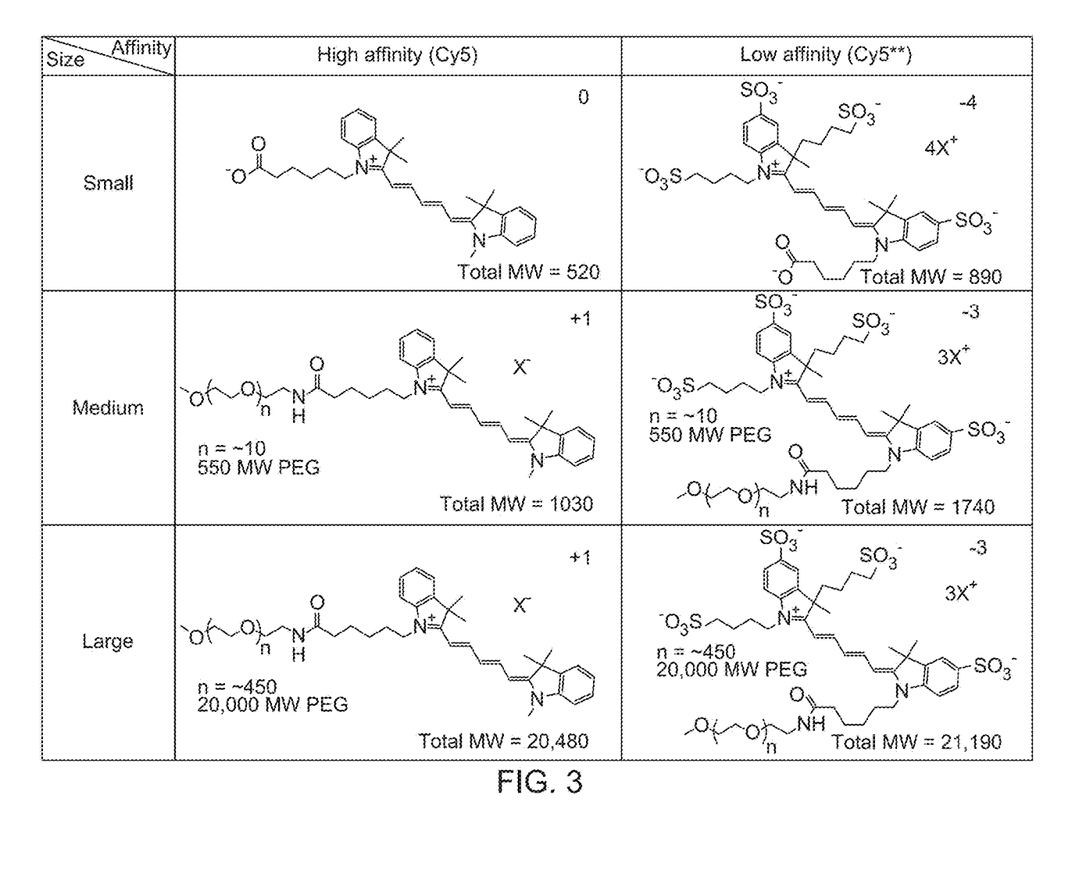
FIG. 3 depicts chemical structures of molecules under study, in accordance with aspects of the present disclosure.
Figure 4:
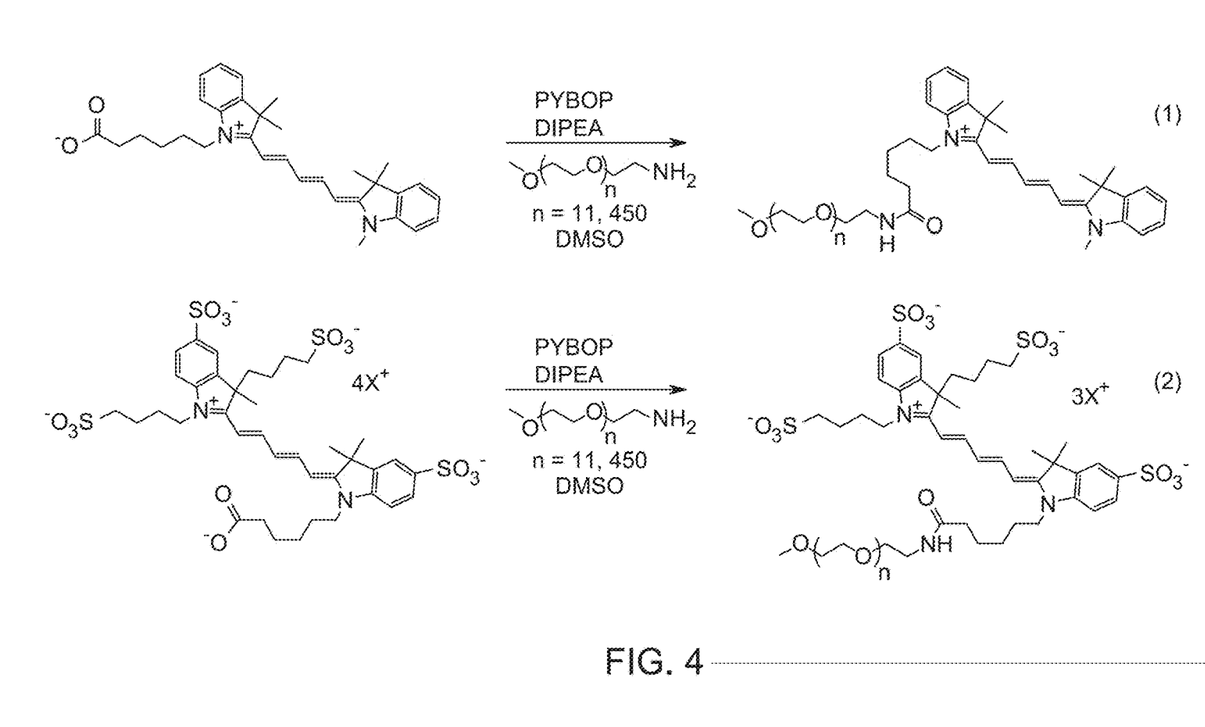
FIG. 4 depicts chemical reactions used to produce certain of the molecules of FIG. 3.

Turning to FIG. 3, examples of molecules which were investigated are shown. The molecules investigated included the Cy5 and Cy5 free acids (referred to as Cy5COOH and Cy5COOH) as well as derivatives substituted with polyethyleneglycol (PEG) (to modify the size of the target) having average molecular weights of 550 g/mole and 20,000 g/mole. The Cy5COOH was commercially available and the Cy5COOH was synthesized by GE Healthcare. The pegylated molecules were synthesized from the respective free acids as shown in equations 1 and 2 of FIG. 4. The absorption maxima were determined to be different for the two classes of Cy5 dyes. Studies indicated that the optimal excitation wavelength to achieve maximum fluorescence intensity for the unsulfonated Cy5 is 640 nm (with emission at 655 nm) and for Cy5 it is 650 nm (with emission at 670 nm). The quantum yield of unsulfonated Cy5 has been determined to be 1.6 times that of Cy5**.

Figure 5:
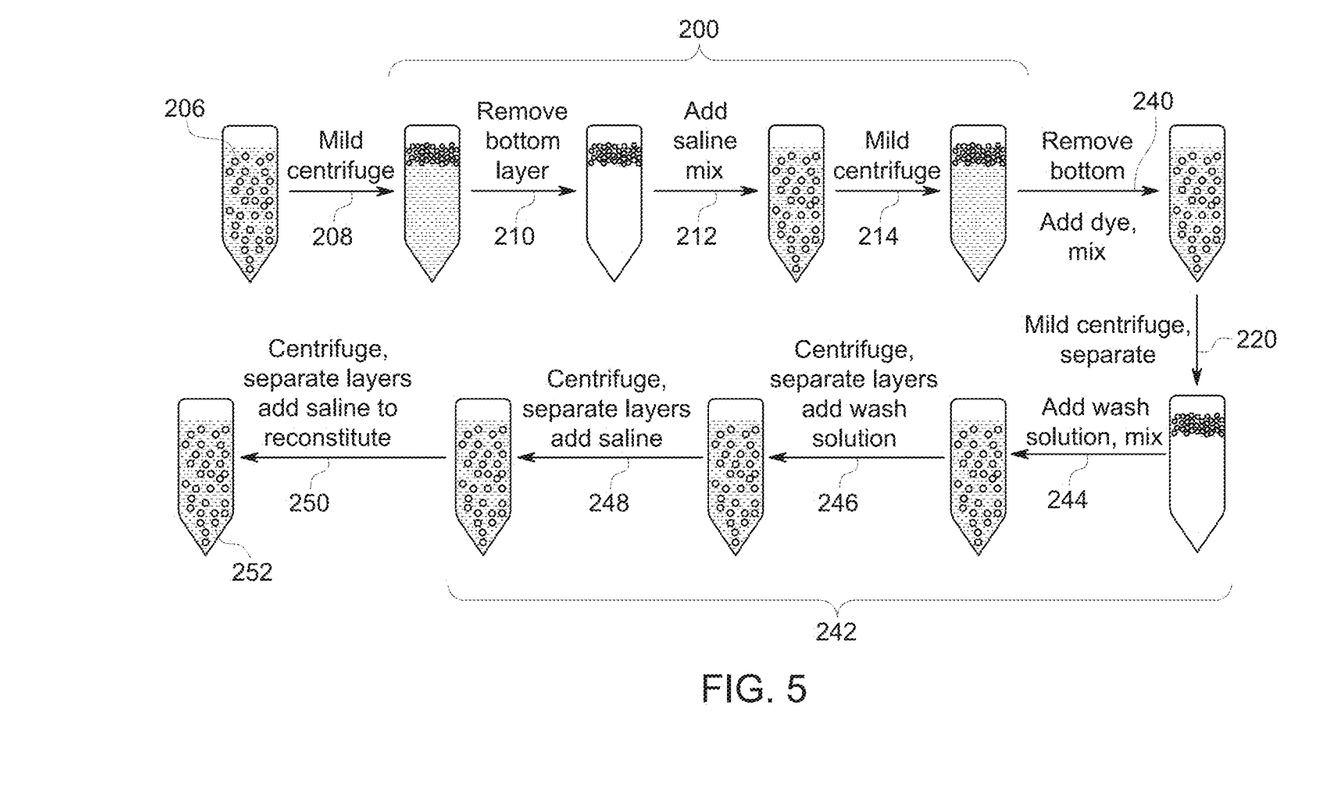
FIG. 5 depicts a further sample preparation process flow, in accordance with one aspect of the present disclosure.

In the studies, dye/bubble mixtures using Cy5 were prepared as shown in FIG. 5. In the depicted process, three operations are shown. In the first operation (steps 200), bubble separation and a wash to remove free albumin were performed. In the second operation (step 240), the washed bubbles were mixed with the dye binding solution. In the third operation (steps 242), a sequence of wash steps were performed followed by saline reconstitution (step 250) to afford the final composition for analysis.

With respect to the first operation, in this example, Optison™ was used as the microbubble composition 206, and it was washed once with saline (step 212) to remove free HSA present in the commercial product. In particular, in the depicted example, the microbubble product 206 was initially centrifuged (step 208), the bottom layer removed (step 210), saline added and mixed (step 212), followed by an additional centrifugation (step 214). After centrifugation the bottom layer was again removed, and to the remaining albumin microbubbles was mixed the Cy5 dye composition (step 240). In the tested scenarios, the Cy5 derivative of interest and the albumin microbubble formulation were mixed at room temperature. The product derived from mixing the dye solution and microbubbles was centrifuged (step 220).

The resulting microbubble/dye product was washed (steps 244, 246, 248) with one or more wash solutions. A variety of wash scenarios were tested. In the first scenario, three saline washes were performed. In the second scenario, two denatured HSA washings and one saline wash were performed. In the third scenario, two native HSA washes and one saline wash were performed. Protein washes contained 9.5 mg/mL HSA. The denatured HSA used in these experiments was soluble, homogeneous HSA isolated from commercial Optison™ product. The washed product was reconstituted in saline (step 250) to yield the final analytic product 252.

The resulting analytic products 252 were used to assess the binding affinity between the Cy5 derivatives and the albumin microbubbles. In particular, in certain studies two complementary fluorescence-based approaches were used to characterize binding in the final dye/microbubble mixtures: fluorescence microscopy and flow cytometry.

In the fluorescence microscopy approach, images from multiple fields of view were acquired and segmented, the background intensity was subtracted, and the number, size, and brightness of the remaining features were calculated. These measured values were believed to correspond to the Cy5 dye bound to the imaged microbubbles.

In the flow cytometry approach, microbubbles pass through a laser intercept one at a time as a consequence of hydrodynamic focusing. The microbubbles scatter the laser light, which is registered as an event. Any fluorescent molecules (e.g., the Cy5 dye derivatives) associated with a given microbubble absorb the laser light and the resulting fluorescence is measured. Fluorescence is only measured when there is a corresponding scattering event. In the present studies, the excitation wavelength employed was 633 nm, and differences in quantum yields between the Cy5 molecules and the Cy5** compounds was taken into account.

Figure 6:
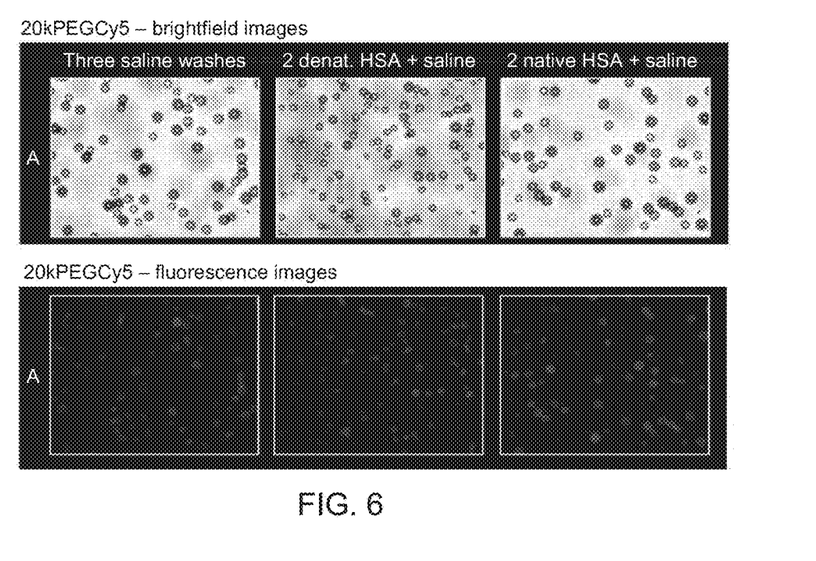
FIG. 6 depicts gray scale representations of brightfield and fluorescence microscopy results for a first composition, in accordance with aspects of the present disclosure.
Figure 7:
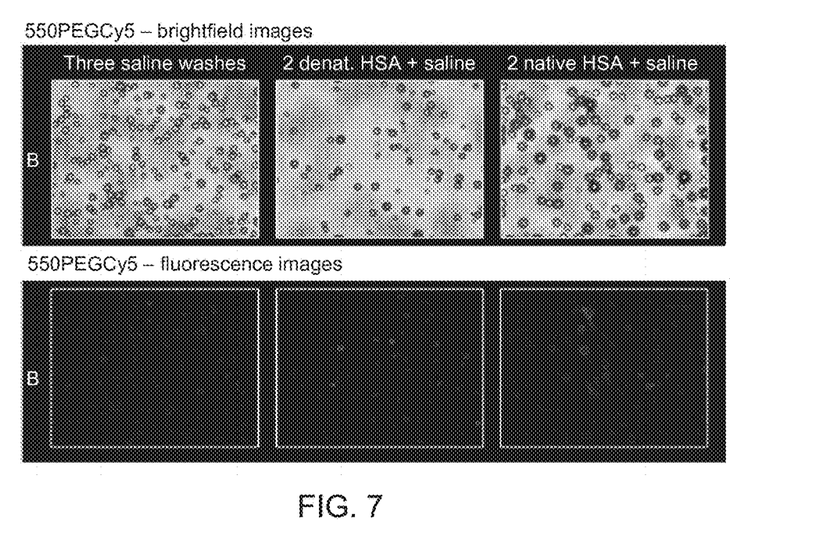
FIG. 7 depicts gray scale representations of brightfield and fluorescence microscopy results for a second composition, in accordance with aspects of the present disclosure.
Figure 8:
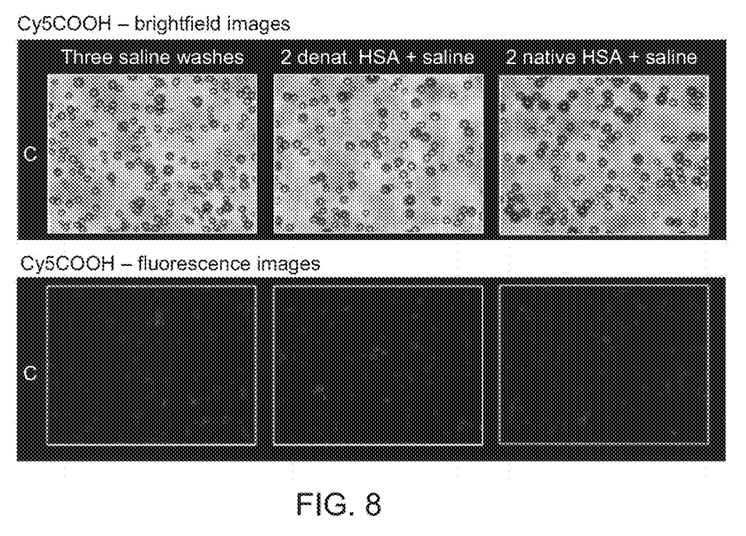
FIG. 8 depicts gray scale representations of brightfield and fluorescence microscopy results for a third composition, in accordance with aspects of the present disclosure.
Figure 9:
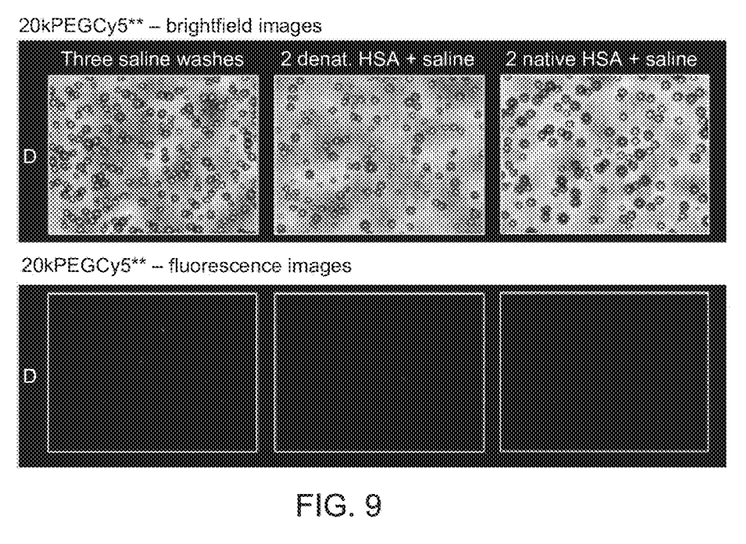
FIG. 9 depicts gray scale representations of brightfield and fluorescence microscopy results for a fourth composition, in accordance with aspects of the present disclosure.
Figure 10:
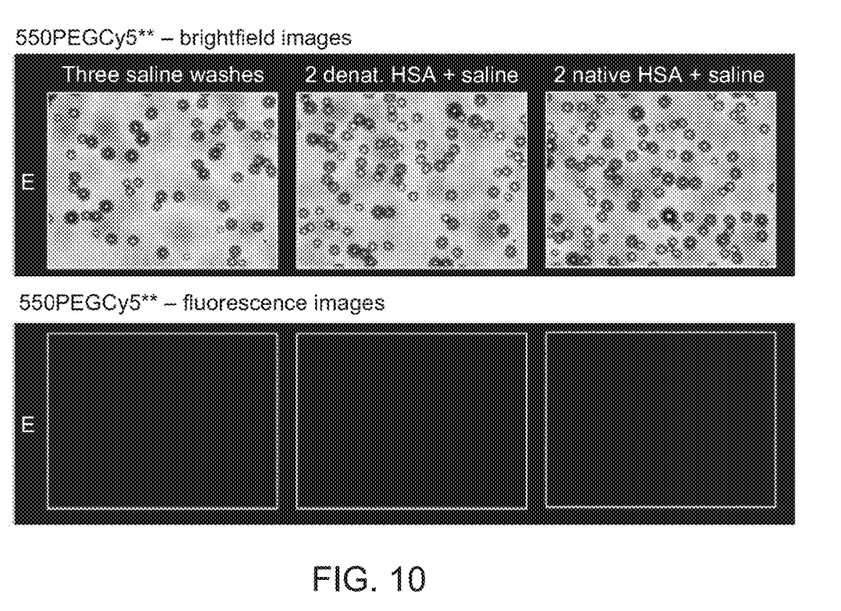
FIG. 10 depicts gray scale representations of brightfield and fluorescence microscopy results for a fifth composition, in accordance with aspects of the present disclosure.

FIGS. 6-10 depict the resulting brightfield and fluorescence images of the albumin microbubble and Cy5 dye mixtures. The fluorescence images (bottom row images) were captured after subtraction of the background signal, as noted above. FIG. 6 depicts images acquired using the 20 k PEG Cy5 moiety; FIG. 7 depicts images acquired using the 550 PEG Cy5 moiety; FIG. 8 depicts images acquired using the Cy5 COOH moiety; FIG. 9 depicts images acquired using the 20 k PEG Cy5 moiety; and FIG. 10 depicts images acquired using the 550 PEG Cy5 moiety.

Figure 11:
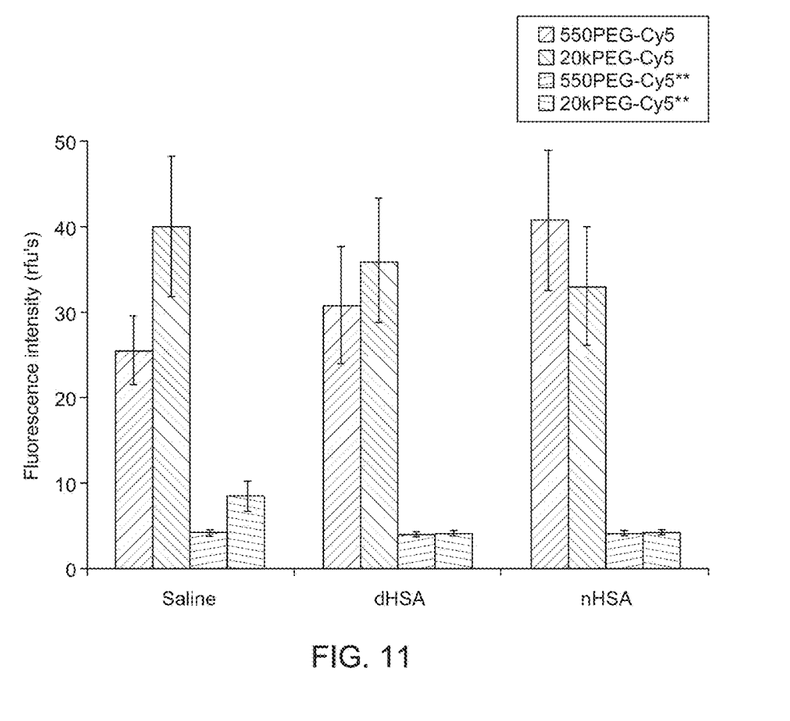
FIG. 11 depicts a graphical representation of fluorescence microscopy results, in accordance with aspects of the present disclosure.

As shown, each fluorescence image was captured in the same field of view as the corresponding brightfield image above it. Using images captured in multiple fields of view, the average fluorescence intensity of each bubble after subtracting the background signal was calculated for each mixing/washing scenario. A graphical summary of calculated values is shown in FIG. 11. In the graphical summary, the respective error bars correspond to ±1 standard deviation. As can be seen in the reproduced images, the Cy5 derivatives exhibited persistent binding. Conversely, the weaker binding Cy5** compounds were easily washed away from the bubbles.

Figure 12:
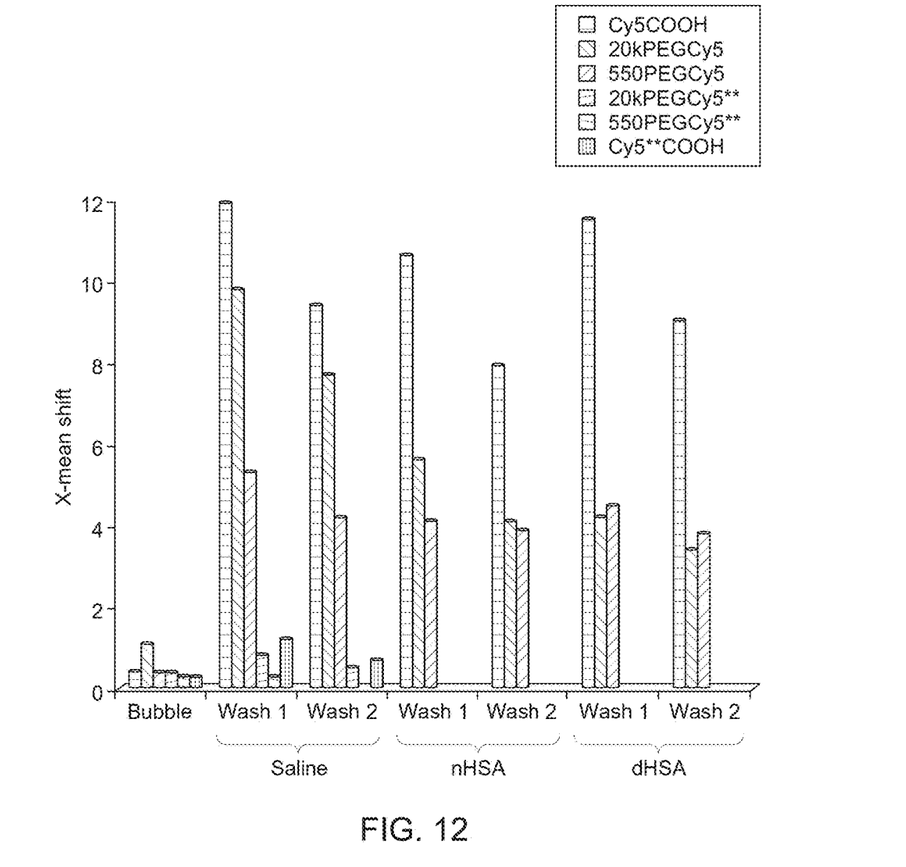
FIG. 12 depicts a graphical representation of flow cytometry results, in accordance with aspects of the present disclosure.

With respect to the flow cytometry results, flow cytometry was used to characterize binding in mixtures of albumin microbubbles and Cy5 dye derivatives both before and after the various washing routines, as described above. The results of the flow cytometry study are graphically summarized in FIG. 12, where characterization of the microbubble/dye mixtures is shown as a function of wash cycles and where "nHSA" corresponds to native human serum albumin and "dHSA" corresponds to denatured human serum albumin.

Consistent with the fluorescence microscopy studies, the flow cytometry results indicate that derivatives comprising the hydrophobic Cy5 show binding to the microbubbles which persists through saline and protein washes. Conversely, the hydrophilic Cy5** derivatives are present in a much lower concentration in washed samples. In particular, in the flow cytometry results, under all wash conditions, the smallest most hydrophobic dye, the Cy5COOH, showed the highest level of bubble binding. Consistent with the fluorescence microscopy results, the 20kPEGCy5 showed greater binding than the 550PEGCy5 following saline washes, but they were essentially equivalent following protein washes.

As will be appreciated, in all of the fluorescence microscopy and flow cytometry studies described, dye/microbubble washings were performed with either saline solutions or solutions of HSA. Generally, it was observed that the Cy5 derivatives bound persistently to the bubble through wash cycles employing not only saline, but also native and denatured HSA. Further, persistent binding of Cy5 derivatives was observed when washes were performed using human blood serum or whole (rat) blood. In particular, it was observed overall that unsulfonated Cy5 bound measurably and durably to albumin microbubbles.

In the examples described herein, the albumin binding moiety was mixed with the albumin microbubbles after microbubble manufacture. As will be appreciated, however, the albumin binding moiety may be present at or included in the microbubble manufacturing process so as to be present in or bound to the microbubble product. That is, these steps need not be separate and discrete, though they are discussed as such in the present document so as to simplify explanation. Thus, implementations in which the albumin binding moiety is incorporated into the bubble manufacturing process are also considered within the scope of this disclosure.

To gain additional insight into the extent to which the Cy5 and Cy5** derivatives bind to albumin microbubbles, a series of equilibrium studies were performed. Aspects of these studies helped to: (1) characterize system behavior under conditions more relevant to the in vivo experiment, i.e. in the presence of a large excess of native HSA, and (2) characterize the relative affinity that fluorescent agents of interest have for HSA in microbubbles compared to native HSA. In these experiments, different albumin concentrations (native or present in microbubbles) were treated with a fixed concentration of dye (i.e., Cy5 derivative). The albumin/dye mixtures were centrifuge filtered to separate bound dye from unbound, and the fluorescence of the unbound dye was measured using a plate reader.

Figure 13:
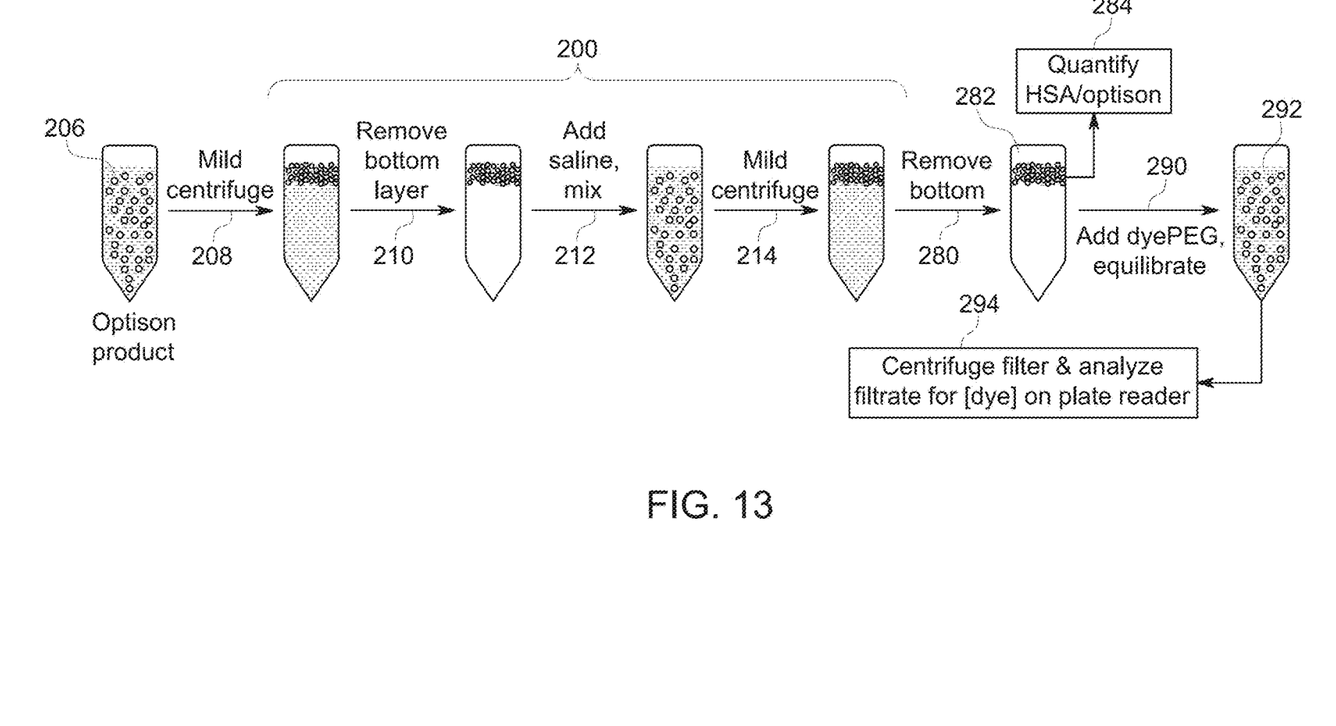
FIG. 13 depicts a further sample preparation process flow, in accordance with aspects of the present disclosure.

The sample preparation method for the experiments using bubbles is summarized in FIG. 13. With respect to the sample preparation steps, bubble separation and a wash to remove free albumin (steps 200) were performed. In this example, the microbubble product 206 was initially centrifuged (step 208), the bottom layer removed (step 210), saline added and mixed (step 212), followed by an additional centrifugation (step 214). After centrifugation the bottom layer was again removed (step 280) to yield a microbubble product 282. To perform the equilibrium calculations, a quantification step 284 was performed on the microbubble product 282 prior to adding (step 290) the respective Cy5 derivative under investigation. The resulting microbubble/dye composition 292 was then centrifuged, filtered, and analyzed on a plate reader (step 294).

With respect to the binding equilibrium between the dye and the microbubbles, the equilibrium equation:

$$X = n^{*}[\text{HSA}]/(K_d + [\text{HSA}]) \quad (1)$$

was employed, where X is the fraction of ligand bound (based on observed fluorescence), and n is the number of binding sites per HSA. In the equilibrium expression, n (e.g., the number of Cy5 or Cy5** binding sites) is assumed to be 1.

With the preceding in mind, the fraction of the 20 k PEG Cy5 dye bound to native HSA was measured over a range of albumin concentrations and compared to the binding fraction measured in mixtures of the dye with albumin microbubbles. The results are shown graphically in FIG. 14 which depicts the dye (e.g. Cy5) binding fraction profiles as a function of native HSA concentration (on the left) and as a function of microbubble albumin concentration (on the right). The corresponding calculated equilibrium constants are shown in Table 1 below, where the ratio is the ratio of binding constant to microbubble albumin versus free native HSA and where HSA (microbubble) refers to the albumin that makes up the albumin microbubble. Kd denotes the dissociation constant, and Ka denotes the association constant.

TABLE 1

| Agent | | HSA | HSA (microbubble) | Ratio |
|---|---|---|---|---|
| 20k PEG Cy5 | $K_d$ (μM) | 1.4 ± 0.2 | 0.3 ± 0.1 | ~4.5 |
| | $K_a$ (μM) | 0.7 | 3.3 | |
| 20k PEG Cy5** | $K_d$ (μM) | 2.2 ± 0.4 | 0.5 ± 0.0 | ~4.5 |
| | $K_a$ (μM) | 0.46 | 2 | |

Figure 14:
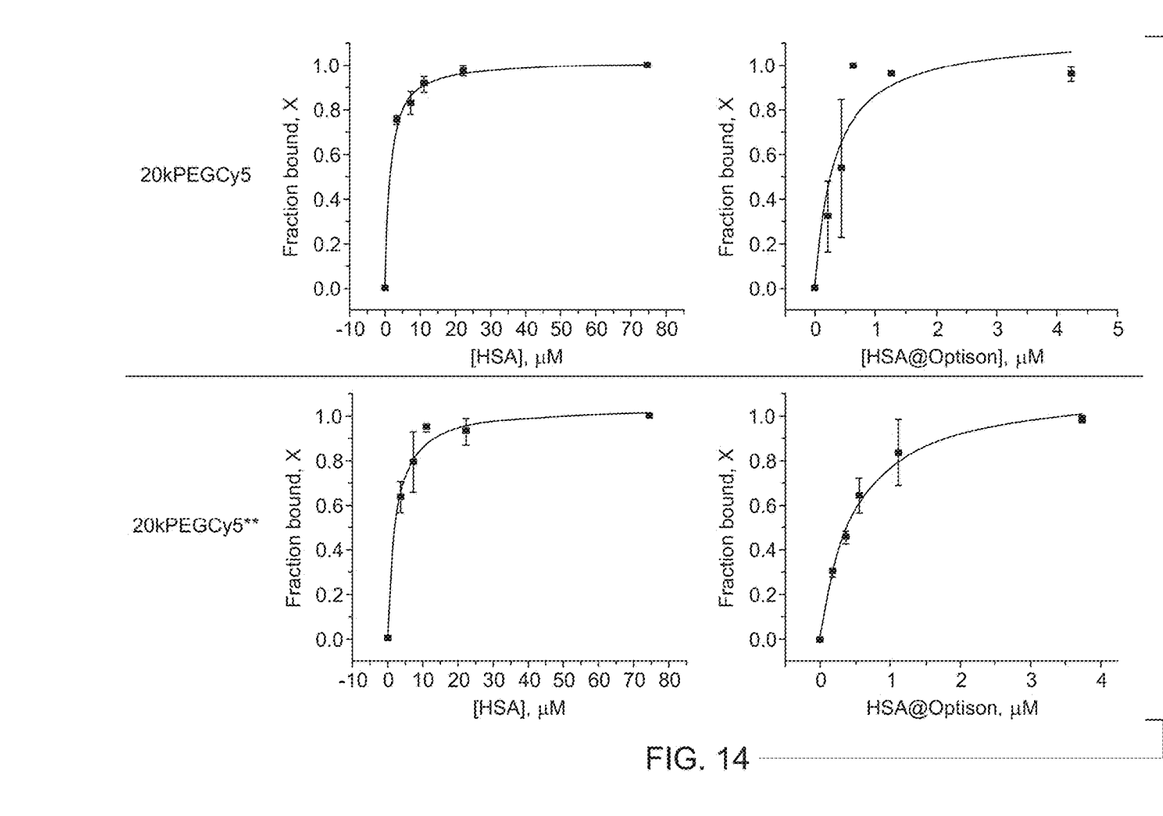
FIG. 14 depicts graphical representations of dye binding fraction profiles as a function of native HSA concentration and as a function of microbubble albumin concentration, in accordance with aspects of the present disclosure.

As can be seen both in FIG. 14 and Table 1, the binding constant for [dye/albumin in the microbubble shell] is more than 4.0 times higher than it is for [dye/native HSA] for both the 20kPEGCy5 and the weaker binder 20kPEGCy5. This is a surprising result in that the binding substrate in both instances is albumin, with the only distinction being that albumin in the form of a microbubble shell is preferentially bound relative to free, native HSA. This will likely affect the equilibrium distribution or partitioning of dye between the bubbles and free albumin in the blood stream. As will be appreciated, other degrees of binding preference (e.g., greater than 2.0 or greater than 3.0) may also be of significance and useful for preferentially binding a therapeutic or diagnostic agent to albumin microbubbles. As the data presented shows, while both the 20kPEGCy5 and the 20kPEGCy5 showed a binding preference for albumin microbubbles vs free native albumin, they did not show the same persistence in binding to microbubbles, for example, after washing (FIGS. 6-10). In some embodiments, the stronger binding unsulfonated Cy5 derivatives may be preferred. In other embodiments, the weaker binding highly sulfonated Cy5** derivatives may be preferred.

Calculations based on these results suggest that, under acceptable in vivo test conditions (e.g., 1 mL of 2.5 µM dye mixed with 1 mL of albumin microbubble product), each microbubble contains on average about 420,000 bound dye molecules when the dye is 20kPEGCy5. On average, about 5.5% of all bubble albumin molecules have a 20kPEGCy5 bound to them. In contrast, under the same conditions, when the dye is 20kPEGCy5**, there are on average about 160,000 dye molecules bound to each bubble, with about 2.2% of all bubble albumin associated with the dye.

In view of these results, therapeutic and/or diagnostic agents of different sizes may be attached to albumin microbubbles using a moiety (e.g., a "tether" molecule) that exhibits preferential binding to the albumin microbubble (e.g., non-native HSA or partially denatured and partially crosslinked HSA) relative to free, native HSA. Without being limited by theory, the long range structure of albumin molecules in the bubble shell, driven by intramolecular and intermolecular arrangement as well as bubble surface shape, may also play a role in observed binding preferences. In certain embodiments, the moiety (e.g., Cy5 or a Cy5 derivative) may be provided as a functional group on the therapeutic or diagnostic agent of interest, either as an added group or a group intrinsically present on the agent of interest. In other embodiments, the therapeutic or diagnostic agent comprises as part of its chemical structure a moiety which is not Cy5 or a Cy5 derivative but which has a binding preference for albumin in microbubbles vs free native albumin. Any of these combinations of albumin microbubble, binding moiety (intrinsic or added), and agent may be used in an ultrasound microbubble (USMB) mediated agent delivery system.

Figure 15:
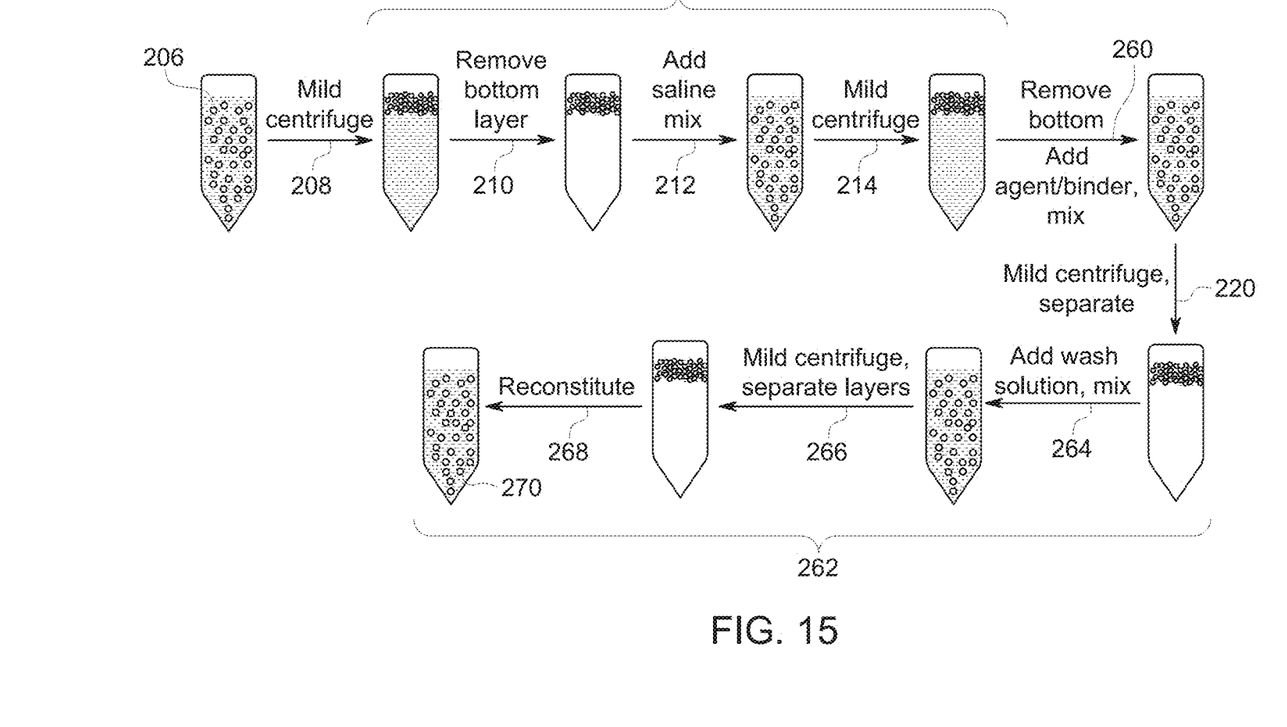
FIG. 15 illustrates another sample preparation process flow which may be used to prepare therapeutic compositions in accordance with aspects of the present disclosure.

One embodiment for preparing such therapeutic compositions is shown in FIG. 15. In the depicted example, an optional wash step 200 may be performed to remove free albumin before the agent/binder is added (step 260). The product is subsequently, optionally washed (steps 262) with another composition, such as saline solution, to substantially remove unbound agent/binder before administration to the subject (e.g., wash step 264 and separation step 266). In other embodiments, additional washes are conducted. In yet other embodiments, no washes are conducted. In embodiments where washes are conducted after the addition of the agent/binder, the composition may then be reconstituted (step 268), such as using saline, to generate the therapeutic product 270 for administration to a patient.

As discussed herein, in certain embodiments the moiety exhibiting a binding preference may act as an optical tracer (e.g., a fluorescent tag). In such embodiments, the optical or fluorescent properties of the moiety may be used in diagnostic applications, such as to monitor or visualize the location of the bound microbubbles relative to an anatomic region of interest, such as during a USMB procedure. Examples of moieties that exhibit preferential binding to albumin microbubbles (relative to free, native HSA) include, but are not limited to Cy5 derivatives.

Technical effects of the invention include a composition of albumin microbubbles to which are bound one or more moieties that exhibit a binding preference for the albumin microbubbles relative to free, native HSA. The one or more moieties may be functionalized with a therapeutic or diagnostic agent. Other technical effects include performing an ultrasound microbubble mediated agent delivery using the albumin microbubbles bound with the moiety.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A composition, comprising:
a microbubble comprising an albumin shell;
a therapeutic agent or a diagnostic agent; and
a moiety bound to the microbubble and to the therapeutic agent or the diagnostic agent, wherein the moiety hydrophobically binds preferentially to the microbubble relative to native albumin, and wherein the moeity is a cyanine 5 derivative comprising polyethyleneglycol units.

2. The composition of claim 1, wherein the therapeutic agent or the diagnostic agent comprises a small molecule drug, an oligonucleotide, or a large molecule.

3. The composition of claim 1, wherein the albumin shell comprises partially denatured, partially cross-linked human serum albumin.

4. The composition of claim 1, wherein the microbubble comprises a perfluoropropane core.

5. The composition of claim 1, wherein the microbubble has a diameter between about 1 µm to about 10 µm.

6. A composition, comprising:
a microbubble comprising an albumin shell;
a therapeutic agent or a diagnostic agent; and
a moiety bound to the microbubble and to the therapeutic agent or the diagnostic agent, wherein the moiety hydrophobically binds preferentially to the microbubble relative to native albumin, wherein the moeity is a cyanine 5 derivative, and wherein the cyanine 5 derivative comprises the following structure:

(I)

7. The composition of claim 1, wherein the cyanine 5 derivative comprises the following structures:

wherein n is 10, or wherein n is 450.

\* \* \* \* \*